United States Patent [19]
Shroff et al.

[11] 4,022,783
[45] May 10, 1977

[54] PIPERAZINYL-IMIDAZOLINES

[75] Inventors: James R. Shroff, Riverside, Conn.; Peter P. Cervoni, New Rochelle, N.Y.

[73] Assignee: USV Pharmaceutical Corporation, Tuckahoe, N.Y.

[22] Filed: Dec. 18, 1975

[21] Appl. No.: 641,966

Related U.S. Application Data

[63] Continuation-in-part of Ser. No. 518,242, Oct. 29, 1975, abandoned.

[52] U.S. Cl. .......................... 260/268 H; 424/250
[51] Int. Cl.$^2$ ............. C07D 401/04; C07D 401/06
[58] Field of Search ................. 260/268 PH, 268 H

[56] References Cited

OTHER PUBLICATIONS

Das et al. J. of Medicinal Chemistry vol. 14, No. 9 pp. 890–891, (1971).
Arya et al. J. of Pharmaceutical Sciences pp. 432–440 vol. 58, (1969).

*Primary Examiner*—Donald G. Daus
*Assistant Examiner*—Jose Tovar
*Attorney, Agent, or Firm*—Leon E. Tenenbaum

[57] ABSTRACT

Compounds of the structure

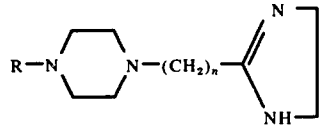

wherein R is lower alkyl or

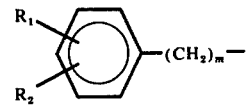

wherein $R_1$ and $R_2$ are hydrogen, lower alkyl, lower alkoxy, hydroxy, amino, nitro, halogen and trifluoromethyl and may be the same or different, and $m$ and $n$ are integers from 0 to 1 have potent hypotensive activity.

11 Claims, No Drawings

PIPERAZINYL-IMIDAZOLINES

This application is a continuation-in-part of patent application Ser. No. 518,242, filed Oct. 29, 1975, now abandoned.

This invention relates to new organic compounds having valuable pharmacological activity and to processes for the preparation of said compounds. In particular, the invention relates to substituted piperazinyl-imidazolines of the formula

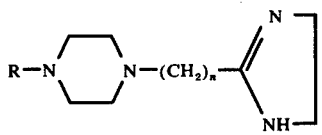

and their pharmaceutically acceptable, non-toxic mono- and di-acid addition salts, wherein R is an alkyl group containing from 1 to 6 carbon atoms or a radical of the formula

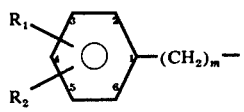

wherein $R_1$ and $R_2$ are hydrogen, lower alkyl, lower alkoxy, hydroxy, amino, nitro, halogen and trifluoromethyl, and may be the same or different, and m is a integer from 0 to 6, and n is an integer from 0 to 1.

The lower alkyl and lower alkoxy groups contain from 1 to 6 carbon atoms and may be straight chained or branched. The lower alkyl groups include methyl, ethyl, isopropyl, butyl, sec-butyl, isobutyl, amyl, isoamyl, hexyl and the like. The alkyl group is preferably straight chained, and when one of $R_1$ and $R_2$ is either a branched alkyl or trifluromethyl the other of $R_1$ and $R_2$ is hydrogen.

The lower alkoxy groups include methoxy, ethoxy, propoxy, isopropoxy, butoxy, amyloxy and the like. The halogen may be fluorine, chlorine, bromine or iodine, and is preferably chlorine or bromine.

Preferably, m is 0 or 1.

Suitable acids used in forming the acid addition salts of the compounds of the present invention include hydrochloric, hydrobromic, phosphoric, sulfuric, acetic, propionic, benzoic, p-hydroxybenzoic, salicylic, mandelic, cinnamic, succinic, citric, malic, maleic, fumaric, tartaric, nicotinic and the like.

According to a process of the invention, the substituted piperazinyl-imidazolines were prepared by the reaction of an appropriately substituted piperazine of the formula

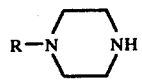

wherein R is as defined above with 2-methylmercaptoimidazoline hydrochloride. The reaction is carried out by refluxing in an inert solvent such as benzene, toluene, dioxane, alkanols, such as methanol, ethanol, isopropanol, butanol, and the like and dimethylformamide. The preferred solvent is dimethylformamide. The products are obtained as their monohydrochlorides which are readily crystallized. The free bases may be obtained from the monohydrochloride by the addition of a suitable alkali such as an alkali or alkaline earth metal hydroxide, carbonate or bicarbonate. The free bases may then be converted to other mono- and diacid addition salts by treatment with the required amount of the desired acid. The intermediate phenylpiperazines were prepared by heating a mixture of morpholine hydrochloride and an appropriately substituted aniline hydrochloride for 4 to 8 hours at 230° to 240° C. according to the procedure of Teruichu Fujii, et al, Japanese Pat. No. 7231 Nov. 4, 1954).

The intermediate phenyl piperazines were also prepared by reaction of the appropriately substituted aniline with bischloroethyl amine in xylene at an elevated temperature.

The methylmercaptoimidazoline hydrochloride was prepared by passing methyl chloride into a solution of commercially available 2-mercaptoimidazoline in dimethylformamide.

In another process of the present invention the substituted piperazinyl-imidazolines were prepared by the reaction of the appropriately substituted piperazine with a 2-halomethyl-imidazoline, such as the 2-chloromethyl imidazoline which was obtained according to the method described in U.S. Pat. No. 2,252,723.

The invention will be more fully understood from the following example which is given by way of illustration and is not to be considered as limiting.

EXAMPLE 1

1-(3,4-Dichlorophenyl) -4-(2-imidazolino)-piperazine Dihydrochloride.

A solution of 10.3 gms. (0.0067 mole) of 2-methyl-mercaptomidazoline hydrochloride and 15.6 gms. (0.067 mole) of 3,4-dichlorophenylpiperazine in 60 ml of dry dimethylformamide was refluxed for a period of 16 – 18 hours. The solution was cooled slightly and 18 ml of 4.9 N hydrochloric acid added. On cooling, the desired hydrochloride salt was obtained. It was filtered, and the crude material recrystallized twice from 95% methanol to yield 9.3 gms. of product, m.p. 220°–222°.

EXAMPLE 2

1-(2,6-Diclorophenyl)-4-(2imidazolinomethyl) piperazine hydrochloride.

A solution of 3.8 gms (0.025 mole)2-chloromethylimidazoline and 5.7 gms. (0.025 mole) 2,6-dichlorophenylpiperazine in 10 ml dimethylformamide was stirred for a period of 1½ hours at room temperature. Ethyl acetate (25 ml) was added and the reaction mixture stirred for an additional two hours. The desired hydrochloride salt was obtained as a thick precipitate. It was filtered, and the crude material recrystallized twice form isopropanol to yield 1.8 gms. (20%) m.p. 265°–270°.

Following the procedures of the above examples, the following additional compounds were prepared:

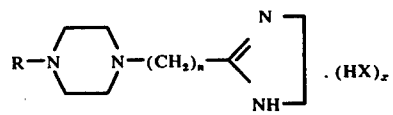

a. where R is

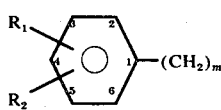

| $R_1$ | $R_2$ | m | n | x | HX | mp° C |
|---|---|---|---|---|---|---|
| H | H | 0 | 0 | 2 | HCl | 220–26 |
| 2-Cl | H | 0 | 0 | 1 | HCl | 233–34 |
| 4-Cl | H | 0 | 0 | 1 | HCl | 209–11 |
| 4-F | H | 0 | 0 | 2 | HCl | 194–200 |
| 4-Br | H | 0 | 0 | 2 | HCl | 231–32 |
| 4-NO$_2$ | H | 0 | 0 | 1 | HCl | 133–36 |
| 4-NH$_2$ | H | 0 | 0 | 1 | HCl | 272–77 |
| 3-CF$_3$ | H | 0 | 0 | 2 | HCl | 185–95 |
| 2-Me | H | 0 | 0 | 2 | HCl | 203–05 |
| 2-Me | 6-Me | 0 | 0 | 1 | HCl | 285–89 |
| 2-MeO | H | 0 | 0 | 2 | HCl | 196–98 |
| 2-MeO | 5-MeO | 0 | 0 | 1 | HCl | 300 |
| 3-Br | 4-Br | 0 | 0 | 2 | HCl | 258–62 |
| 3-Cl | 4-Cl | 0 | 0 | 2 | HCl | 220–22 |
| 2-Cl | 3-Cl | 0 | 0 | 1 | HCl | 260–62 |
| 2-Cl | 4-Cl | 0 | 0 | 1 | HCl | 206–07 |
| 2-Cl | 6-Cl | 0 | 0 | 1 | HCl | 300 |
| 3-Cl | 4-Cl | 1 | 0 | 2 | HCl | 260–69 |
| 3-Me | 4-Cl | 0 | 0 | 2 | HCl | 259–70 |
| 3-MeO | 4-Cl | 0 | 0 | 2 | HCl | 225–28 |
| 3-Cl | 4-F | 0 | 0 | 2 | HCl | 178–85 |
| 3-MeO | 4-MeO | 0 | 0 | 1 | HCl | 205–07 |
| 3-EtO | 4-EtO | 0 | 0 | 2 | HCl | 229–39 |
| 3-OH | 4-OH | 0 | 0 | 2 | HBr | 265–70 |
| 2-Cl | 5-Cl | 0 | 0 | 2 | HCl | 219–20 |
| 3-Cl | 5-Cl | 0 | 0 | 2 | HCl | 214–15 |
| 3-Cl | 4-Cl | 0 | 1 | 2 | HCl | 128–30 |
| 2-Cl | H | 0 | 1 | 2 | HCl | 233–34 | b) where R is alkyl

| R | n | x | mp° C |
|---|---|---|---|
| CH$_3$ | 1 | 2 | 254–56 |
| n-C$_6$H$_{13}$ | 1 | 2 | 265–68 |

The compounds of the present invention exhibited long lasting activity in reducing the blood pressure of spontaneous hypertensive rats. In such rats, at a dose of 100mg/kg p.o., the blood pressure was lowered from about 10 to 37% for periods of about 25 – 60 hours. The compounds would, therefore, be useful in the treatment of hypertension.

We claim:

1. A compound selected from the group consisting of compounds of the formula

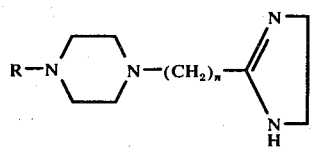

wherein n is an integer from 0 to 1, and R is a radical of the formula

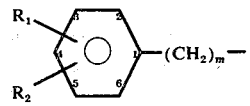

wherein m is an integer from 0 to 1, and $R_1$ and $R_2$ are selected from the group consisting of hydrogen, lower alkyl, lower alkoxy, hydroxy, amino, halogen and trifluromethyl and may be the same or different, with the proviso that when one of $R_1$ or $R_2$ is a branched alkyl or trifluromethyl, the other of $R_1$ and $R_2$ is hydrogen, and their pharmaceutically acceptable, non-toxic mono- and di-acid addition salts.

2. A compound according to claim 1, wherein R is

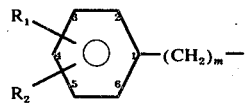

3. A compound according to claim 2 wherein m is 1.
4. A Compound according to claim 3 wherein $R_1$ is hydrogen and $R_2$ is halogen.
5. A compound according to claim 4 wherein $R_2$ is chlorine or bromine.
6. A compound according to claim 3 wherein $R_1$ and $R_2$ are halogen.
7. A compound according to claim 6 wherein $R_1$ and $R_2$ are chlorine
8. A compound according to claim 6 wherein $R_1$ and $R_2$ are bromine
9. A compound according to claim 7 wherein $R_1$ is 3-chloro and $R_2$ is 4-chloro.
10. A compound according to claim 5 wherein $R_2$ is 4-chloro.
11. A compound according to claim 5 wherein $R_2$ is 4-bromo wherein $R_1$, $R_2$ and m are the same as defined in claim 1.

* * * * *